US006680205B1

(12) United States Patent
Elhard et al.

(10) Patent No.: US 6,680,205 B1
(45) Date of Patent: *Jan. 20, 2004

(54) SOLVENT-ACTIVATED COLOR FORMING COMPOSITIONS

(75) Inventors: Joel D. Elhard, Hilliard, OH (US); Richard P. Heggs, Dublin, OH (US)

(73) Assignee: Battelle Memorial Instittue, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/557,733

(22) Filed: Apr. 26, 2000

(51) Int. Cl.$^7$ .................................... G01N 25/56
(52) U.S. Cl. ................ 436/166; 436/169; 422/58; 473/378; 73/73
(58) Field of Search .................. 422/56, 58, 61; 436/39, 1–3, 164, 166, 169; 473/378; 73/73

(56) References Cited

U.S. PATENT DOCUMENTS

| | | | |
|---|---|---|---|
| 3,669,711 A | 6/1972 | Kimura et al. | |
| 3,819,396 A | 6/1974 | Vincent et al. | |
| 3,821,010 A | 6/1974 | Vincent et al. | |
| 4,302,393 A | 11/1981 | Garner et al. | |
| 4,865,813 A | * 9/1989 | Leon | 422/101 |
| 5,130,290 A | 7/1992 | Tanimoto | |
| 5,431,697 A | 7/1995 | Kamata | |
| 5,501,945 A | 3/1996 | Kanakkanatt | |
| 5,779,979 A | * 7/1998 | Berglund et al. | 422/82.09 |
| 5,823,891 A | 10/1998 | Winskowicz | |
| 5,938,544 A | 8/1999 | Winskowicz | |
| 6,071,853 A | 6/2000 | Kirk et al. | |

* cited by examiner

Primary Examiner—Lyle A. Alexander
(74) Attorney, Agent, or Firm—Klaus H. Wiesmann; Courtney J. Miller

(57) ABSTRACT

Color-forming compositions comprising (i) a solvent absorbing material such as a polymer; (ii) a color-former or chelating agent compounded with the solvent absorbing material; and (iii) a source of metal ions, whereby the metal ions complex with the color former as the solvent absorbing material absorbs the solvent, resulting in a detectable color change of the solvent absorbing material. Both reversible and irreversible versions of these color-forming compositions are provided.

2 Claims, 2 Drawing Sheets

SOLVENT-ACTIVATED COLOR FORMING COMPOSITIONS

BACKGROUND OF THE INVENTION

The present invention relates to solvent-activated and solvent-sensitive color forming compositions, their method of making and method of use.

Prolonged exposure to, or immersion in, certain solvents (e.g., water) can adversely affect the physical, chemical and mechanical properties of some polymer materials, composite materials, and synthetic construction materials. For example, the exterior of golf balls typically consists of one or more polymer materials. A golf ball that has been submerged in a water hazard for an extended period of time will exhibit inferior flight characteristics compared to a new golf ball, despite the superficial similarity in appearance of the two golf balls (*Golf Digest,* September 1996). In some instances, the diminished performance of certain materials caused by prolonged exposure to a solvent is temporary and mostly reversible if the solvent is removed by drying the affected materials. In other situations the effects are permanent and performance is irreversibly damaged. In certain situations, any exposure to a solvent, however brief, may create performance concerns. Thus, there is a need for a color-based indicator that can be incorporated into various solvent-sensitive materials which will alert the user to the possibility that the performance of the materials has been compromised by exposure to, or immersion in, a given solvent. Ideally, color formation would be either reversible or permanent based on different formulations of the indicator and the material it is combined with.

Several water-sensitive color systems currently exist. U.S. Pat. No. 5,130,290 to Tanimoto discloses a water-sensitive coloring sheet which includes a substrate and a water-sensitive coloring layer containing an unencapsulated color developing material that reacts with a dye when the coloring layer is wetted. The inclusion of a desensitizing material in this system results in a reversible color formation system (i.e., the removal of water results in the removal of the color). U.S. Pat. No. 5,501,945 to Kanakkanatt discloses the concept of a reversible system in which water sensitive chemichromic dyes are incorporated into polymers used for various packaging applications. U.S. Pat. Nos. 5,823,891 and 5,938,544, both to Winskowicz disclose a color-forming system for use with golf balls which utilizes a water permeable covering over the core of a golf ball, and a water soluble pelletized or microencapsulated colored dye near or within the covering.

All of the discussed systems require some type of colored dye which when subjected to the correct stimulus undergoes a color change. Such dyes must often be processed, i.e., pelletized or microencapsulted, before they can be incorporated into a particular material. Processing dyes in the manner adds difficulty and expense to the process of creating a water-activated color forming material. Furthermore, these dyes may be removed by simply bleaching the colored material.

BRIEF SUMMARY OF THE INVENTION

These, and other deficiencies of the prior art are overcome by the present invention which provides a color-forming composition that includes a solvent absorbing material such as a polymer, a chelating agent or "color former" that is compounded with the solvent absorbing material, and source of metal ions such as zinc acetate. The metal ions form a chelate complex with the color former as a solvent (e.g., water) is absorbed by the polymer resulting in the polymer changing color. The color-forming composition of the present invention is white or colorless after initial processing and does not change color until it has absorbed the solvent. This color-forming composition is essentially "aquachromic" meaning that color change occurs upon exposure to liquid water, but is not "hydrochromic" because exposure to moderate humidity alone does not initiate a color change. Once the color change has occurred, the color-forming composition of this invention is unaffected by treatment with typical solutions designed for color removal for extended periods of time.

Therefore, it is an object of the present invention to provide a color-forming composition that can be used for multiple purposes, including use as the outer cover of golf balls, whereby prolonged exposure of the color-forming composition to a liquid solvent, such as water, results in a detectable color change of the composition.

It is an additional object of the present invention to provide both a reversible and an irreversible color forming composition, whereby the color change is permanent upon the removal of a solvent from the composition, or whereby the color change is temporary, and the color fades from the composition upon removal of the solvent from the composition, but can be regenerated upon repeated exposure to the solvent.

Further objects, advantages, and novel aspects of this invention will become apparent from a consideration of the figures and subsequent detailed description.

DETAILED DESCRIPTION OF THE INVENTION

In general, the present invention provides a color-forming composition that includes a solvent-absorbing material, a chelating agent or "color former" that is compounded with the solvent absorbing material, and a source of metal ions. The metal ions form a chelate complex with the chelating agent or color former as a solvent (e.g. water) is absorbed by the solvent-absorbing material, resulting in a color change of the solvent absorbing material. For example, the solvent-absorbing material may change from white to green, brown, or black. The color-forming composition of the present invention is white or colorless after initial processing, and does not change color until it has absorbed water. Furthermore, the present invention provides a color-forming composition that is essentially "aquachromic" meaning that color change occurs upon exposure to liquid water (or other solvent), but that is not "hydrochromic" because exposure to moderate humidity alone does not initiate a color change. Finally, once the color change has occurred, the color-forming compositions of this invention are unaffected by treatment with typical solutions designed for color removal (e.g., 3% $H_2O_2$, 1M HCl, Alconox, Clorox Bleach) for extended periods of time. Long term exposure to hazardous solvents such as bleach will ultimately degrade the polymer itself, thus the polymer will break down before the color change can be removed.

Figure 1:
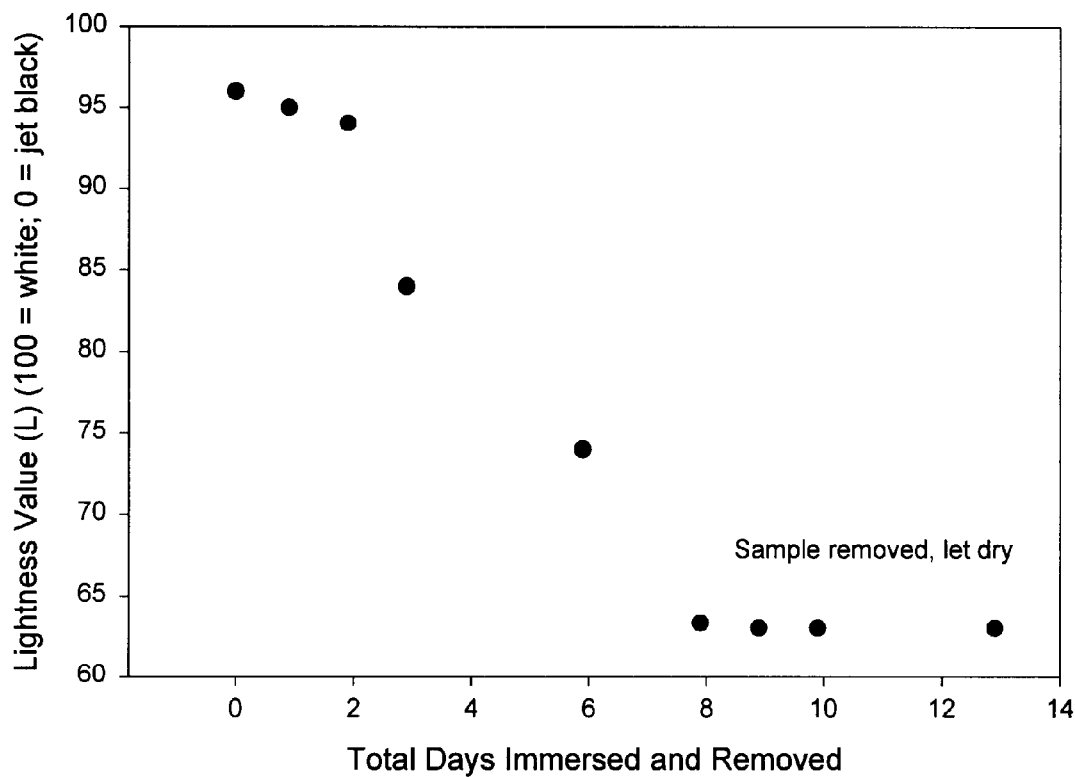
FIG. 1 depicts a color formation vs. time plot for the irreversible color forming embodiment of the present invention. In a typical experimental procedure, samples of each composition are compounded on a 2-roll mill at about 104° C. (220° F.), compression molded into a plaque form, cut to about 2×5 inches size, weighed on an analytical scale, and the initial color measured using a X-rite (L,a,b values). The samples are then immersed in water. Periodically, samples are removed, reweighed, and the color remeasured.

In a preferred embodiment of the present invention, the color-forming composition is used as the outer cover for golf balls, which is typically white. The solvent absorbing material is the polymer polyethylene acrylic acid ionomer containing about 5% titanium dioxide filler (tradename SURLYN), the color former or chelating agent is 1,2-Dihydroxybenzene (also known as Catechol), and the metal ions are zinc (+2) from zinc acetate. In the preferred embodiment, the polymer, the color changer, and the Zn (+2) ions are compounded to form the outer cover of the golf ball. In another embodiment, only Catechol is compounded with the polymer and color former, and the source of metal ions is derived from the ionomer itself, the solvent, or from another source. The preferred solvent is water, and if a golf ball covered with the color-forming composition of the present invention is submersed in water for an extended period of time (e.g. about two to eight days), the polymer absorbs water, thereby moving the Zn (+2) ions (individually or complexed with another material) into contact with the color former, or vice-versa. The metal ions and the color former form a chelate complex which results in a permanent darkening of the outer cover of the golf ball. FIG. 1 provides a representative color formation vs. time plot for the preferred embodiment. In this embodiment, the darkened color cannot be reversed if the water is removed from the outer cover. The performance of the color formation in a particular polymer system can be controlled by the type and loading of both the color former and the corresponding metal ion, where performance includes rate of color formation, final color level achieved, stability (shelf-life) under elevated temperature and humidity conditions, as desired. A preferred formulation for this embodiment includes: polyethylene acrylic acid ionomer or ionomer blend (e.g., 80% Surlyn 8940, 20% Surlyn 9910) containing about 5% titanium dioxide filler resin; and from about 0.15% to 2.0% 1,2-Dihydroxybenzene, and from about 0.25% to 2.0% Zinc acetate. The optimum color formation in these systems is achieved with a stoichiometric ratio of chelating agent and metal ion (e.g. about 1.67:1 Zn Acetate/Catechol or integer multiples thereof).

Adding greater amounts of color forming components (i.e., chelating agent and metal ions) results in increased rapidity and intensity of color formation. Substitution of certain components will also increase rapidity and intensity of color formation; for example, in one embodiment Mg (II) acetate is used place of Zn (II) acetate to create a more rapid color change. In other embodiments of the present invention, certain adjuvants are added to the composition to enhance or inhibit the water absorption of the base polymer and modify the color formation process. These additives include, but are not limited to, pentaerythritol, ethylene glycol, polyethylene glycol, and polyacrylic acid.

A preferred embodiment of the present invention exhibits thermo-oxidative stability at compounding temperatures of at least 104° C. (220° F.) and extrusion temperatures of at least 207° C. (450° F.). This embodiment also exhibits stability against premature color formation under elevated temperature and humidity conditions. For example, representative formulations exposed to 40–45° C. (104–113° F.) and 75% RH (relative humidity) in an environmental chamber for a period of 24 hours show no discernable color change (less than about 1 L unit). Similarly, materials exposed to milder, ambient-like conditions (e.g., about 72° F./45% RH) show no discernable change for at least a week, compared to the substantial color development (40–50 L units) over the same period of water immersion.

For purposes of example, Catechol complexed with Fe(+3) has the following expected structure:

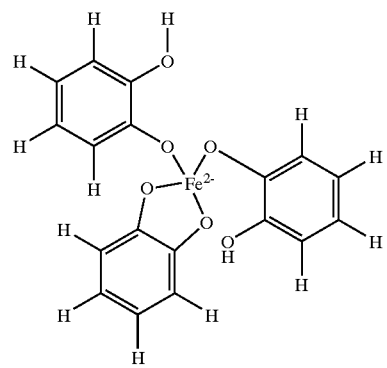

Alternatively, the chelate-complex may be present in a form where the additional ligands (e.g. acetate and hydrate forms) also participate, as shown for the Zinc (II) diacetate dihydrate-catechol complex below:

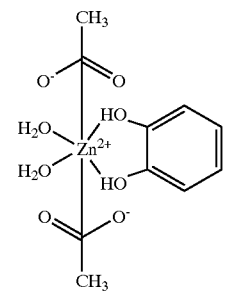

Figure 2A:
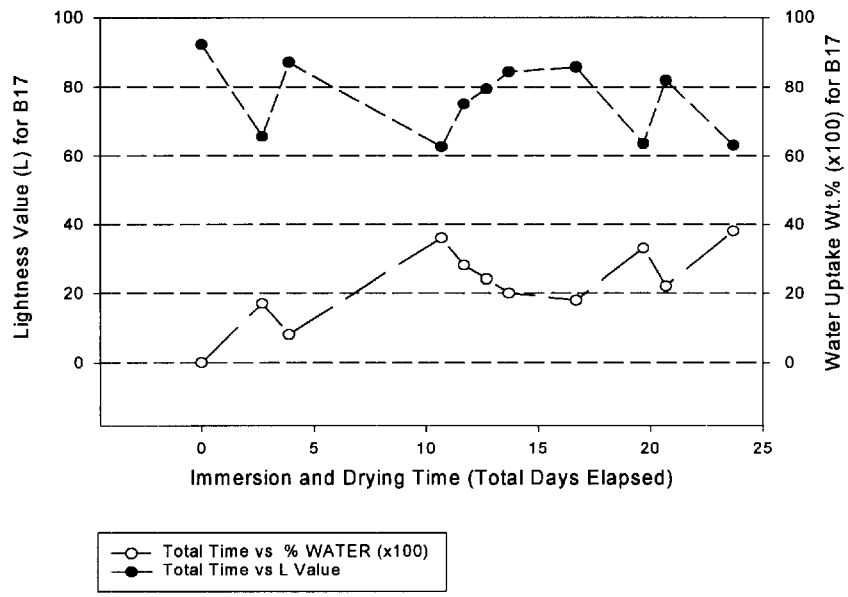
FIG. 2a depicts a color formation vs. time plot for the reversible color forming embodiment of the present invention before an extrusion check for thermo-oxidative stability. See the legend for FIG. 1 for a description of analytical test procedures.
Figure 2B:
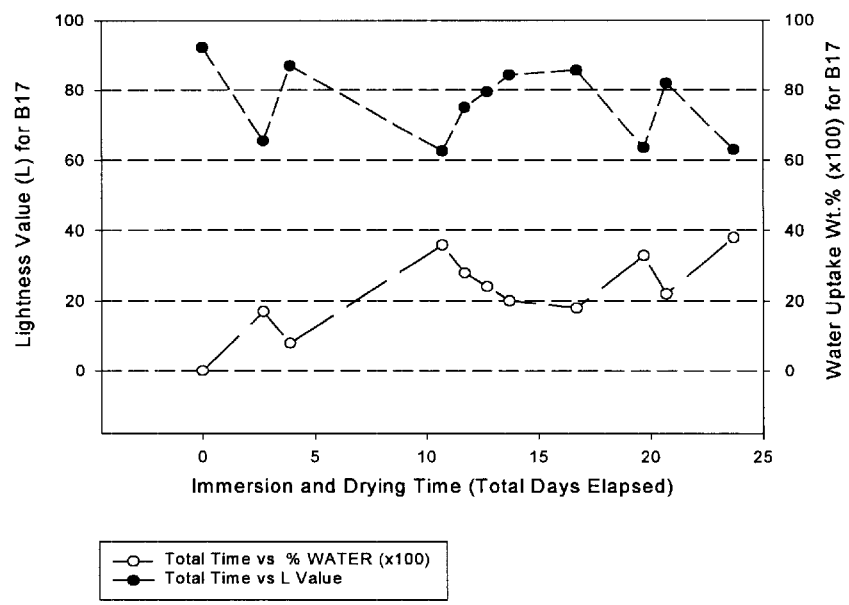
FIG. 2b depicts a color formation vs. time plot for the reversible color-forming embodiment of the present invention after an extrusion check for thermo-oxidative stability. See the legend for FIG. 1 for a description of analytical test procedures.

In an alternate embodiment this invention, the preferred source of metal ions is zinc acetate, and the color former is a diethylaminofluroan-based dye (tradename PERGASCRIPT BLACK I-R). Use of this dye results in the reversible formation of color in the outer cover of the golf ball when absorbed water is removed from the outer cover by drying. In this embodiment, reversibility of the color change is maintained as long as the level of Zn (+2) ionomer in the total composition does not exceed about 50%. A typical preferred formulation for this embodiment includes: about 2 pph polyethylene acrylic acid ionomer containing about 5% titanium dioxide filler resin; about 1 pph diethylaminofluroan based dye resin; and about 2 pph zinc acetate (anhydrous<0.2 wt % water) resin. This embodiment also exhibits thermo-oxidative stability at compounding temperatures of at least 104° C. (220° F.) and extrusion temperatures of at least 207° C. (450° F.). FIG. 2a and FIG. 2b provide color formation versus time plots for the reversible embodiment of the present invention before and after an extrusion check for thermo-oxidative stability. Structures for PERGASCRIPT BLACK I-R (PB-IR) as determined by nuclear magnetic resonance (NMR), and a likely complex with Zn acetate during water immersion are shown below:

of metal ions; (ii) dry blending the solvent-absorbing material, the chelating agent, and the metal ions in a batch process; and (iii) compounding the batch in an extruder or other suitable mixing device. An alternative method of

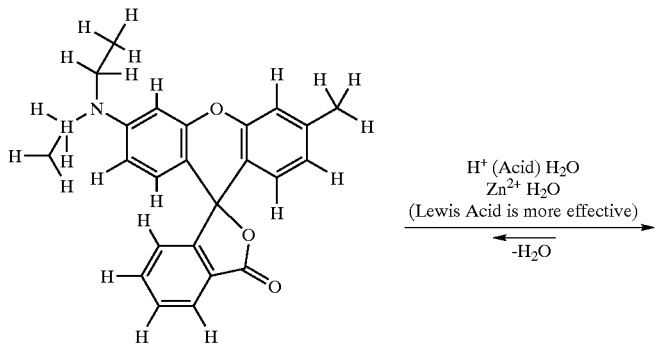

Pergascript PB-IR: Fluoran/Spiropyran Dye (Colorless form), PB-I2R is Dimethyl version

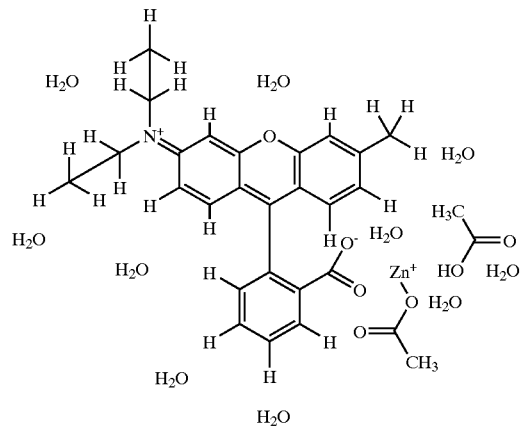

Colored Zwitterionic form (Black for PB-IR), including Zn+2 complex and water molecules In other embodiments of the present invention, the polymer polyethylene acrylic acid is replaced with other polymers including polyurethane, poly-(acrylonitrile-butadiene-styrene), polyvinyl chloride, polypropylene-copolymer, and polystyrene or combinations thereof. These polymers are widely used in a number of industrial and packaging applications. In alternate embodiments, the solvent absorbing material is paint, or synthetic construction material such as polyvinyl chloride, polyurethane, silicone elastomers, or organic rubbers.

In other embodiments of the present invention, the solvent is an inorganic solvent such as ammonium hydroxide, hydrogen peroxide, hydrochloric acid, or hypochlorite (bleach); or an organic solvent such as ethanol, ethyl acetate, toluene, xylene, or diesel fuel. Preferred organic solvents are those exhibiting some degree of polarity such as ethyl acetate and tetrahydorfuran.

In alternate embodiments where color formation is irreversible, the color former is selected from aromatic di-hydroxy compounds such as 3-Methylcatechol, 4-Methylcatechol, and 4,5-Dihydroxy 1,3-benzenedisulfonic acid disodium salt (Tiron), or alternatively, 1,2,3-Trihydroxybenzene (pyrogallol). In an alternative embodiment where color formation is reversible, the color former is the dimethylamino analog PERGASCRIPT BLACK I-2R.

The source of metal ions may vary widely in alternative embodiments. For example, in one embodiment, the source of metal ions is the solvent itself. In another embodiment, the source of metal ions is the solvent-absorbing material. In still another embodiment the source of the metal ions is any one of a variety of metal salts. In alternative embodiments, the metal ions themselves are Zn (+2), Fe (+3), Na (+), Ca (+2), Mg (+2), Li (+), Ti (+2), Mn (+2), or any other suitable metal ion, both as isolated cations and with other coordinating ligands such as hydrate, acetate, or ester forms (e.g., Zn(II) 3,5-di-t-butylsalicylate).

One method of making a color-forming composition of the present invention includes the steps of: (i) providing a solvent-absorbing material, a chelating agent, and a source making a color-forming composition, includes the steps of (a) providing a solvent-absorbing material, a chelating agent, and a source of metal ions; and (ii) metering the solvent-absorbing material, the chelating agent, and the metal ions into an extruder or other continuously compounding device. Another method of making a color-forming composition includes dry blending or continuously metering the active ingredients into the final processing step, provided that the final processing step has a minimum amount of mixing capability such as provided by an injection molder or an extruder.

A preferred method for making a color-forming composition, which utilizes a "masterbatch" includes the steps of: (i) providing a solvent-absorbing material, a chelating agent, and a source of metal ions; and (ii) at the final fabrication step, adding the chelating agent and the source of metal ions to the solvent absorbing material at a level higher than that required for the desired final concentration of the chelating agent and the source of metal ions in the solvent-absorbing material. For example, a pigment masterbatch may contain 40% pigment by weight, while the final product may only contain 4% or less. In this embodiment, the masterbatch is mixed with the base resin at the final fabrication step such as injection molding in a ratio that results in the final desired additive amount.

The benefits of the masterbatch approach include the following: (i) additives can be handled in the "neat" or 100% concentrated state at a remote location for safety or other reasons such as the need for special handling equipment (as in the case of liquid additives) or the desire to minimize the risk of contamination of other products; (ii) the masterbatches improve dispersion of the additive in the final product by being processed twice (many final fabrication processes typically optimize the plastication or melting of the polymer rather than optimize mixing); (iii) additives are sensitive to environmental degradation such as moisture or light the small volume of masterbatch can be more easily protected and handled; (iv) a resin of different characteristics can be used for the masterbatch and the final product to improve processing. For example, the masterbatch resin could be lower in viscosity to increase the amount of additive it can contain while the resin for the final part may be higher in viscosity to improve mechanical properties; and (v) masterbatches can use very aggressive and expensive mixing equipment such as twin screw extruders while the final product can use equipment suited to the formation of the part.

While the above description contains many specificities, these should not be construed as limitations on the scope of the invention, but rather as exemplification of preferred embodiments. Numerous other variations of the present invention are possible, and it is not intended herein to mention all of the possible equivalent forms or ramifications of this invention. Various changes may be made to the present invention without departing from the scope of this invention.

What is claimed is:

1. A solvent-activated, color-forming composition, comprising:

(a) a solvent-absorbing material;

(b) a color former compounded with said solvent-absorbing material, wherein said color former is a chelating agent; and (c) a source of metal ions compounded with said solvent-absorbing material or said solvent-absorbing material containing the metal ions wherein metal ions from said source of metal ions are capable of complexing with said color former as said solvent-absorbing material absorbs said solvent, resulting in a detectable color change of said solvent-absorbing material; and wherein said solvent-absorbing material is polyethylene acrylic acid ionomer containing about 5% titanium dioxide filler resin; said color former is about 0.15% to 2.0% 1,2-Dihydroxybenzene; and said source of compounded metal ions is about 0.25% to 2.0% zinc acetate.

2. A color-forming composition, comprising:

(a) a solvent-absorbing material;

(b) a color former compounded with said solvent-absorbing material, wherein said color former is a chelating agent;

(c) a source of metal ions compounded with said solvent-absorbing material or said solvent-absorbing material containing the metal ions;

said solvent absorbing material is a polymer or a polymer composite, wherein said polymer comprises polyethylene acrylic acid ionomer containing about 5% titanium dioxide filler resin.

* * * * *